US006503270B1

(12) United States Patent
Richter et al.

(10) Patent No.: US 6,503,270 B1
(45) Date of Patent: *Jan. 7, 2003

(54) SERPENTINE COILED LADDER STENT

(75) Inventors: Jacob Richter, Ramat Hasharon (IL); Gregory Pinchasik, Herzeliya (IL)

(73) Assignee: Medinol Ltd., Tel Aviv (IL)

( * ) Notice: Subject to any disclaimer, the term of this patent is extended or adjusted under 35 U.S.C. 154(b) by 196 days.

This patent is subject to a terminal disclaimer.

(21) Appl. No.: 09/587,994

(22) Filed: Jun. 6, 2000

Related U.S. Application Data

(63) Continuation-in-part of application No. 09/204,771, filed on Dec. 3, 1998, now Pat. No. 6,355,059.

(51) Int. Cl.[7] .................................................. A61F 2/06
(52) U.S. Cl. ..................................... 623/1.15; 623/1.22
(58) Field of Search ................................. 623/1.1, 1.15, 623/1.22; 606/191, 151; 24/20 R, 26

(56) References Cited

U.S. PATENT DOCUMENTS

| 4,553,545 A |   | 11/1985 | Maass et al. |
|---|---|---|---|
| 4,649,922 A |   | 3/1987 | Wiktor |
| 4,733,665 A |   | 3/1988 | Palmaz |
| 4,760,849 A | * | 8/1988 | Kropf ........................... 606/191 |
| 4,800,882 A |   | 1/1989 | Gianturco |
| 4,856,516 A |   | 8/1989 | Hillstead |

(List continued on next page.)

FOREIGN PATENT DOCUMENTS

| FR | 2 760 351 | 9/1998 |
|---|---|---|
| WO | WO98/30173 | 7/1998 |
| WO | 98/38945 | 9/1998 |

OTHER PUBLICATIONS

D. Maass et al., "Radiological Follow–Up Of Transluminally Inserted Vascular Endoprostheses: An Experimental Study Using Expanding Spirals," Radiology 1984; 152: 659–663.

Primary Examiner—David O. Reip
Assistant Examiner—Julian W. Woo
(74) Attorney, Agent, or Firm—Kenyon & Kenyon

(57) ABSTRACT

A serpentine coiled ladder stent is provided, in which the coil is formed from a wound strip of cells, wherein the sides of the cells are serpentine. Thus, the stent is comprised of a strip helically wound into a series of coiled windings, wherein the strip is formed of at least two side bands connected to each other, for example by a series of cross struts. The cross struts may be positioned slightly askew. Each side band is formed in a serpentine pattern comprising a series of bends, wherein upon expansion of the stent, the bends of the side bands open to increase the length of each of the individual cells in the helical direction, thereby lengthening the strip in the helical direction to allow the stent to expand without any significant unwinding of the strip.

20 Claims, 5 Drawing Sheets

U.S. PATENT DOCUMENTS

| | | |
|---|---|---|
| 4,886,062 A | 12/1989 | Wiktor |
| 4,913,141 A | 4/1990 | Hillstead |
| 4,969,458 A | 11/1990 | Wiktor |
| 5,019,090 A | 5/1991 | Pinchuk |
| 5,102,417 A | 4/1992 | Palmaz |
| 5,104,404 A | 4/1992 | Wolff |
| 5,108,417 A | 4/1992 | Sawyer |
| 5,116,365 A | 5/1992 | Hillstead |
| 5,133,732 A | 7/1992 | Wiktor |
| 5,135,536 A | 8/1992 | Hillstead |
| 5,161,547 A | 11/1992 | Tower |
| 5,282,824 A | 2/1994 | Gianturco |
| 5,314,472 A | 5/1994 | Fontaine |
| 5,383,892 A | 1/1995 | Cardon et al. |
| 5,449,373 A | 9/1995 | Pinchasik et al. |
| 5,514,154 A * | 5/1996 | Lau et al. .................. 623/1.15 |
| 5,613,981 A | 3/1997 | Boyle et al. |
| 5,707,387 A | 1/1998 | Wijay |
| 5,716,396 A * | 2/1998 | Williams, Jr. ................. 623/1.1 |
| 5,733,303 A | 3/1998 | Israel et al. |
| 5,800,520 A | 9/1998 | Fogarty |
| 5,810,872 A | 9/1998 | Kanesaka et al. |
| 5,824,052 A | 10/1998 | Khosravi et al. |
| 5,824,053 A | 10/1998 | Khosravi et al. |
| 5,843,168 A | 12/1998 | Dang |
| 5,925,061 A | 7/1999 | Ogi et al. |
| 5,931,867 A | 8/1999 | Haindl |
| 5,961,548 A | 10/1999 | Shmulewitz |
| 6,355,059 B1 * | 3/2002 | Richter et al. ............. 623/1.22 |

* cited by examiner

SERPENTINE COILED LADDER STENT

CROSS-REFERENCE TO RELATED APPLICATION

This application is a continuation-in-part of prior U.S. patent application Ser. No. 09/204,771, filed Dec. 3, 1998 now U.S. Pat. No. 6,355,059.

FIELD OF THE INVENTION

The invention relates generally to stents, which are endoprostheses implanted into vessels within the body, such as blood vessels, to support and hold open the vessels, or to secure and support other endoprostheses in the vessels.

BACKGROUND OF THE INVENTION

Various stents are known in the art. Typically stents are generally tubular in shape, and are expandable from a relatively small, unexpanded diameter to a larger, expanded diameter. For implantation, the stent is typically mounted on the end of a catheter, with the stent being held on the catheter at its relatively small, unexpanded diameter. By the catheter, the unexpanded stent is directed through the lumen to the intended implantation site. Once the stent is at the intended implantation site, it is expanded, typically either by an internal force, for example by inflating a balloon on the inside of the stent, or by allowing the stent to self-expand, for example by removing a sleeve from around a self-expanding stent, allowing the stent to expand outwardly. In either case, the expanded stent resists the tendency of the vessel to narrow, thereby maintaining the vessel's patency.

Some examples of patents relating to stents include U.S. Pat. No. 4,553,545 to Maass et al.; U.S. Pat. No. 4,733,665 to Palmaz; U.S. Pat. Nos. 4,800,882 and 5,282,824 to Gianturco; U.S. Pat. Nos. 4,856,516, 4,913,141, 5,116,365 and 5,135,536 to Hillstead; U.S. Pat. Nos. 4,649,922, 4,886,062, 4,969,458 and 5,133,732 to Wiktor; U.S. Pat. No. 5,019,090 to Pinchuk; U.S. Pat. No. 5,102,417 to Palmaz and Schatz; U.S. Pat. No. 5,104,404 to Wolff; U.S. Pat. No. 5,161,547 to Tower; U.S. Pat. No. 5,383,892 to Cardon et al.; U.S. Pat. No. 5,449,373 to Pinchasik et al.; and U.S. Pat. No. 5,733,303 to Israel et al.

U.S. Pat. No. 4,553,545 to Maass et al. (the "Maass '545 patent"), the disclosure of which is hereby expressly incorporated by reference into this application, shows various stents in the form of coiled springs. FIGS. 1 through 7 of that patent illustrate coiled spring stents formed of helically wound wire wherein the diameters of the stents are contracted and expanded by rotating the spring ends. Such coiled spring stents are very flexible, such that they can be tracked easily down tortuous lumens and such that they conform relatively closely to the compliance of the vessel after deployment. However, while these stents are very flexible, they also lend relatively unstable support after expansion. The individual windings of the coil may move relative to each other, causing sometimes significant gaps between adjacent windings, which could cause significant portions of the vessel wall to be left unsupported. Also, the windings of the coil may bend or tilt somewhat, potentially obstructing and seriously compromising the lumen. FIG. 10 of the Maass '545 patent illustrates an example of tilted windings in these coiled spring stents.

The Maass '545 patent discloses various mechanisms designed to address the instability of these coiled spring stents. For example, FIGS. 11 through 14 show the use of rigidifying devices in the form of axial support members that extend along a side of the stent and maintain the relative positioning of the windings. FIG. 22 shows a stent constructed of a coiled band, wherein the band has openings in it so that it takes the shape of a ladder. FIG. 23 shows another coiled ladder stent, wherein the ladder is formed by two wires attached to each other by transverse elements. Each of these coiled ladder stents provides improved stability when compared to the single strand coiled spring stents.

Despite these modifications, one problem with each of the coiled spring and coiled ladder stents disclosed in the Maass '545 patent is that expansion of the stent results in an unwinding of the coil. This unwinding causes twisting of the stent, including rotation of the stent ends, which is potentially harmful to the vessel wall. In addition, the expansion and twisting causes the number of individual windings to lessen, resulting in less windings to support the vessel wall. The reduction in windings also means either that the length of the stent will foreshorten significantly, in order to maintain the spacing of the windings, or that the spacing between the windings will increase significantly, in order to maintain the length of the stent, or in some instances a combination of both. The foreshortening results in less lengthwise coverage of the vessel wall in the deployed stent as well as lateral movement during deployment which may be harmful to the vessel wall. The increase in the spacing between windings could result in significant portions of the vessel wall being left unsupported. Both are potential disadvantages of the coiled spring and coiled ladder stents disclosed in the Maass '545 patent.

U.S. Pat. Nos. 4,886,062 and 5,133,732 to Wiktor (the "Wiktor '062 patent" and the "Wiktor '732 patent"), the disclosures of which are hereby expressly incorporated by reference into this application, show stents formed of wire wherein the wire is initially formed into a band of zig-zags forming a serpentine pattern, and then the zig-zag band is coiled into a helical stent. The stents are expanded by an internal force, for example by inflating a balloon. Another example of a similar coiled zig-zag stent is the Crossflex stent marketed by Cordis Corporation.

The coiled zig-zag stents that are illustrated in FIGS. 1 through 6 of the Wiktor '062 and '732 patents are very flexible, but, again, they are relatively unstable. The Wiktor '732 patent discloses alternative constructions of these coiled zig-zag stents to address their instability. In one example, illustrated in FIG. 7 of that patent, a straight longitudinal wire extends along a side of the stent and is connected to the windings to fix them relative to each other. In another example, illustrated in FIG. 8 of that patent, in various locations around the helix of the stent, a bend in the zig-zag wire is made longer than other bends, so that it can reach and hook around a bend in an adjacent winding of the helix. Each of these constructions results in increased stability of the stent, but each also results in some reduction in the flexibility of the stent.

SUMMARY OF THE INVENTION

An object of the invention is to provide a stent that is longitudinally flexible such that it can easily be tracked down tortuous lumens and does not significantly change the compliance of the vessel after deployment, wherein the stent is relatively stable so that it avoids bending or tilting in a manner that would potentially obstruct the lumen and so that it avoids leaving significant portions of the vessel wall unsupported.

Another object of the present invention is to provide a stent that has little or no twisting or rotation of its ends upon expansion, and that also undergoes little or no foreshortening upon expansion and simultaneously does not result in significant gaps being created between adjacent windings of the stent upon expansion.

In accordance with one embodiment of the invention, a stent is configured as a coiled stent in which the coil is formed from a wound strip of cells, wherein the sides of the cells are serpentine. Thus, the stent is comprised of a strip helically wound into a series of coiled windings, wherein the strip is formed of at least two side bands connected to each other, for example by a series of cross struts. Each side band is formed in a serpentine pattern comprising a series of bends, wherein upon expansion of the stent, the bends of the side bands open to increase the length of each of the individual cells in the helical direction, thereby lengthening the strip in the helical direction to allow the stent to expand without any significant unwinding of the strip.

A serpentine coiled ladder stent according to the invention retains the flexibility associated with coiled spring stents, yet has windings which are relatively stable and insusceptible to displacement or tilt. A serpentine coiled ladder stent according to the invention thus provides continuous support of the vessel tissue without disadvantageously obstructing the lumen.

In addition, the serpentine coiled ladder stent substantially avoids the problems of twisting, end rotation, foreshortening and the creation of significant gaps upon expansion. When the serpentine coiled ladder stent is expanded, the outward radial force on the stent causes the bends in the serpentine sides to open up and become straighter, thereby causing the overall length of the strip in the helical direction to increase. By providing a serpentine strip that allows the strip itself to lengthen in the helical direction as the stent is expanded, the increase in the diameter of the stent is accommodated by a lengthening of the strip, rather than by an unwinding of the strip. Thus, the number of windings may be maintained, and rotation of the ends and foreshortening or the opening of gaps between windings can be substantially reduced or avoided. In fact, the serpentine coiled ladder stent may be constructed so that adjacent points on adjacent windings remain adjacent to each other as the stent is expanded. Thus, the two ends of the strip at the ends of the stent may be joined, for example by welding, to the respective adjacent windings, thereby creating smooth ends and assuring no relative rotation.

DETAILED DESCRIPTION OF THE ILLUSTRATED EMBODIMENTS

Figure 1:
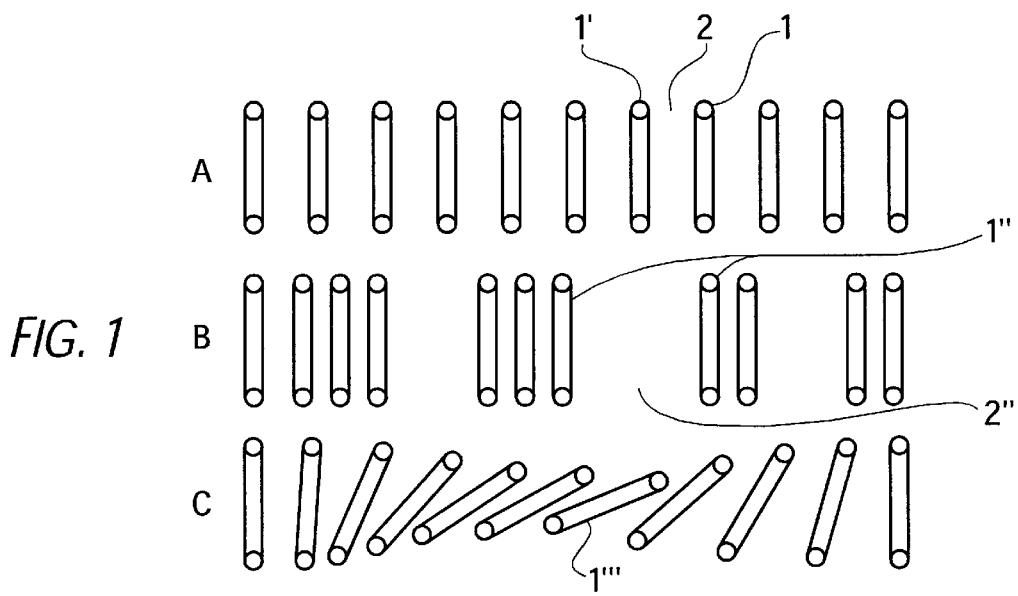
FIG. 1 shows a schematic diagram of three coiled wire stents as in the prior art, the first having equally spaced windings, the second having unevenly spaced windings, and the third have some tilted windings.

FIG. 1 shows a schematic diagram of cross-sections through three prior art stents, each formed of a helically wound wire. The top coiled wire stent A is in its optimal, desired condition, with each of the windings 1' evenly spaced from the next. Thus, the gaps 2' between the adjacent windings 11 are relatively uniform, such that a relatively uniform support is provided to the vessel wall, should the windings 1' remain evenly spaced as shown.

In practice, though, a coiled wire stent as shown in FIG. 1 sometimes tends to change configuration, particularly during and after implantation when it is subjected to various stresses in the vessel. Thus, some of the windings may tend to separate somewhat, as shown in the middle coiled wire stent B in FIG. 1. In the middle coiled wire stent B, the windings 1" are spaced unevenly, sometimes leaving significant gaps 2".

Alternatively or additionally, the windings of the traditional coiled wire stent may bend or tilt while in the vessel. In the bottom coiled wire stent C in FIG. 1, some of the windings 1''' have tilted somewhat. These tilted windings not only fail to provide proper support to the vessel, but they also enter and partially obstruct the passageway through the stent, thus seriously compromising the lumen.

Figure 2:
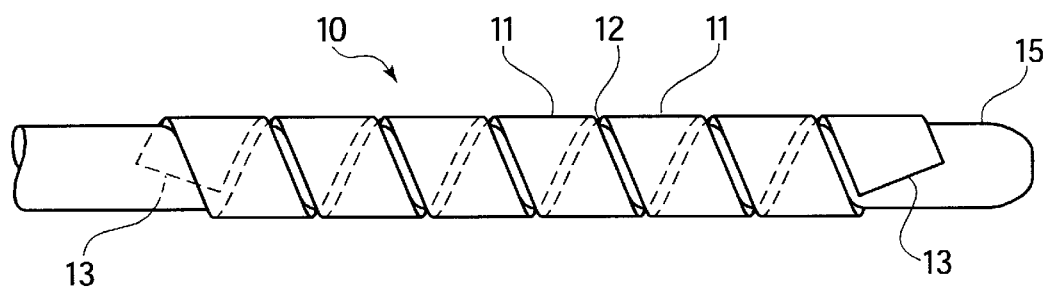
FIG. 2 shows a coiled ribbon stent in an unexpanded condition.

One way to overcome the instability problems of the coiled wire stent is to replace the wire with a ribbon having a width substantially larger than its thickness. FIG. 2 shows an unexpanded coiled ribbon stent 10 mounted on a catheter 15. As shown in FIG. 2, the coiled ribbon stent is formed as a helically wound ribbon strip. Because the width of the ribbon in the coiled ribbon stent 10 as shown in FIG. 2 is greater than the width of the wire in the coiled wire stent A as shown in FIG. 1, the windings 11 of the coiled ribbon stent 10 are relatively resistant to longitudinal displacement or tilting.

Figure 3:
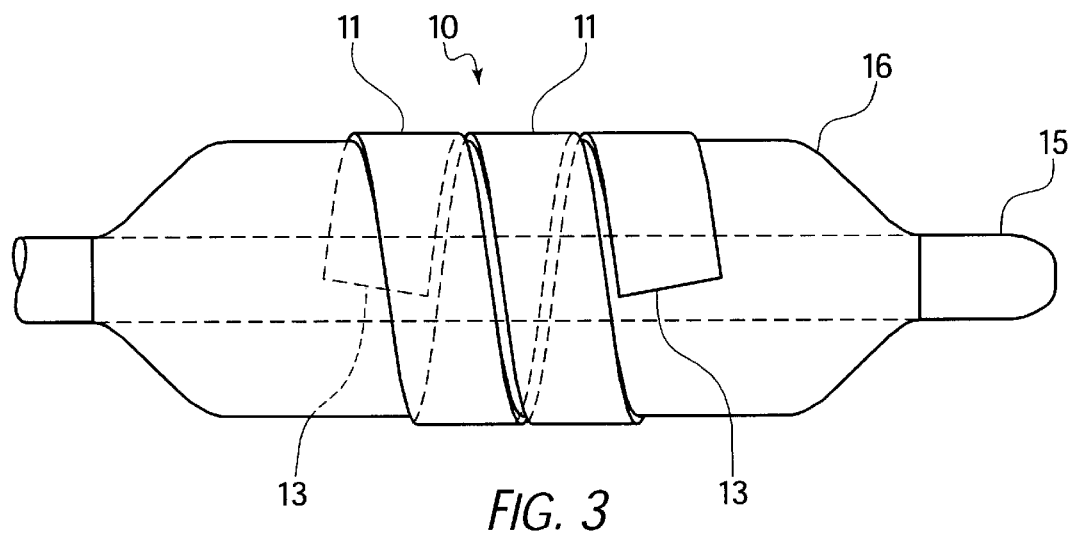
FIG. 3 shows the coiled ribbon stent of FIG. 2 in an expanded condition.

FIG. 3 shows the coiled ribbon stent 10 of FIG. 2 in an expanded condition. Expansion may be accomplished, for example, by inflating a balloon 16 on the catheter 15, with the outward force of the balloon 16 acting on the inside of the stent 10 and causing the stent 10 to expand. When the coiled ribbon stent 10 is expanded as shown in FIG. 3, the diameter of the individual windings 11 increases. However, because the length of the ribbon strip is constant, the increase in diameter causes the ribbon strip to unwind somewhat, in order to accommodate the expansion. In doing so, the ends 13 of the stent 10 rotate, the number of windings 11 decreases, and the overall length of the stent foreshortens and/or gaps are formed between adjacent windings 11. The rotation of the stent, particularly of the stent ends, is potentially harmful to the vessel, and the decrease in windings and the decrease in length of the stent or the opening of significant gaps between windings results in less of the vessel wall being supported and unpredictable lesion coverage.

Figure 4:
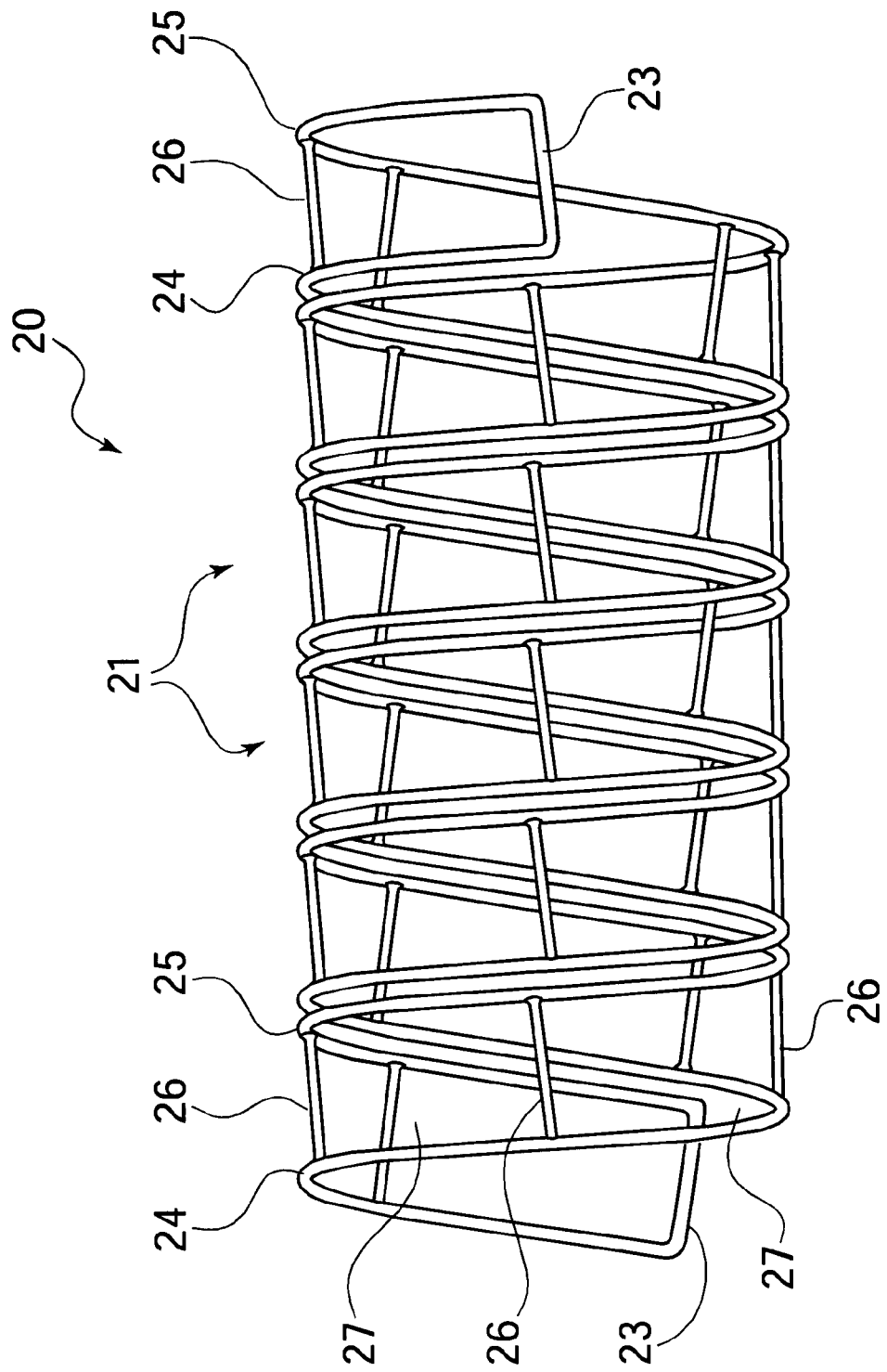
FIG. 4 shows a prior art coiled ladder stent, similar to those shown and described in U.S. Pat. No. 4,553,545 to Maass et al.

In addition to these disadvantages, the coiled ribbon stent 10 is also somewhat disadvantageous in that the metal of the ribbon strip covers a high percentage of the surface area of the stented vessel wall. This high percentage of metal coverage inhibits or slows down the healing response of the vessel wall to the trauma of stenting. This problem of the high percentage of metal coverage in the coiled ribbon stent 10 may be solved by modifying the ribbon strip to a ladder strip, in which the strip coiled to form the stent has a series of openings in it, resembling a ladder. FIG. 4 shows an example of a coiled ladder stent 20, similar to the prior art coiled ladder stents shown and described in U.S. Pat. No. 4,553,545 to Maass et al.

In the coiled ladder stent 20, the strip has side bands 24, 25 bridged by cross struts 26. The side bands 24, 25 and the cross struts 26 form a series of openings 27, in which each opening 27 is bounded by the two side bands 24, 25 and two cross struts 26. Similarly to the coiled wire and the ribbon strip, the ladder strip is wound helically, forming a series of windings 21.

The coiled ladder stent 20 retains the rigidity and stability associated with the coiled ribbon stent 10, since the individual windings 21 of the ladder strip, like the windings 11 of the ribbon strip, have increased width as compared to the individual windings of the coiled wire. In addition, because of the openings 27, the coiled ladder stent 20 yields a reduced area of metal coverage as compared to the coiled ribbon stent 10, without compromising support of the tissue.

The coiled ladder stent 20, however, still has some of the same disadvantages associated with the coiled wire and ribbon stents. Most significantly, the ladder strip unwinds somewhat upon expansion, resulting in twisting of the stent and rotation of the stent ends 23, as well as foreshortening of the stent or the opening of significant gaps between adjacent windings.

Figure 5:
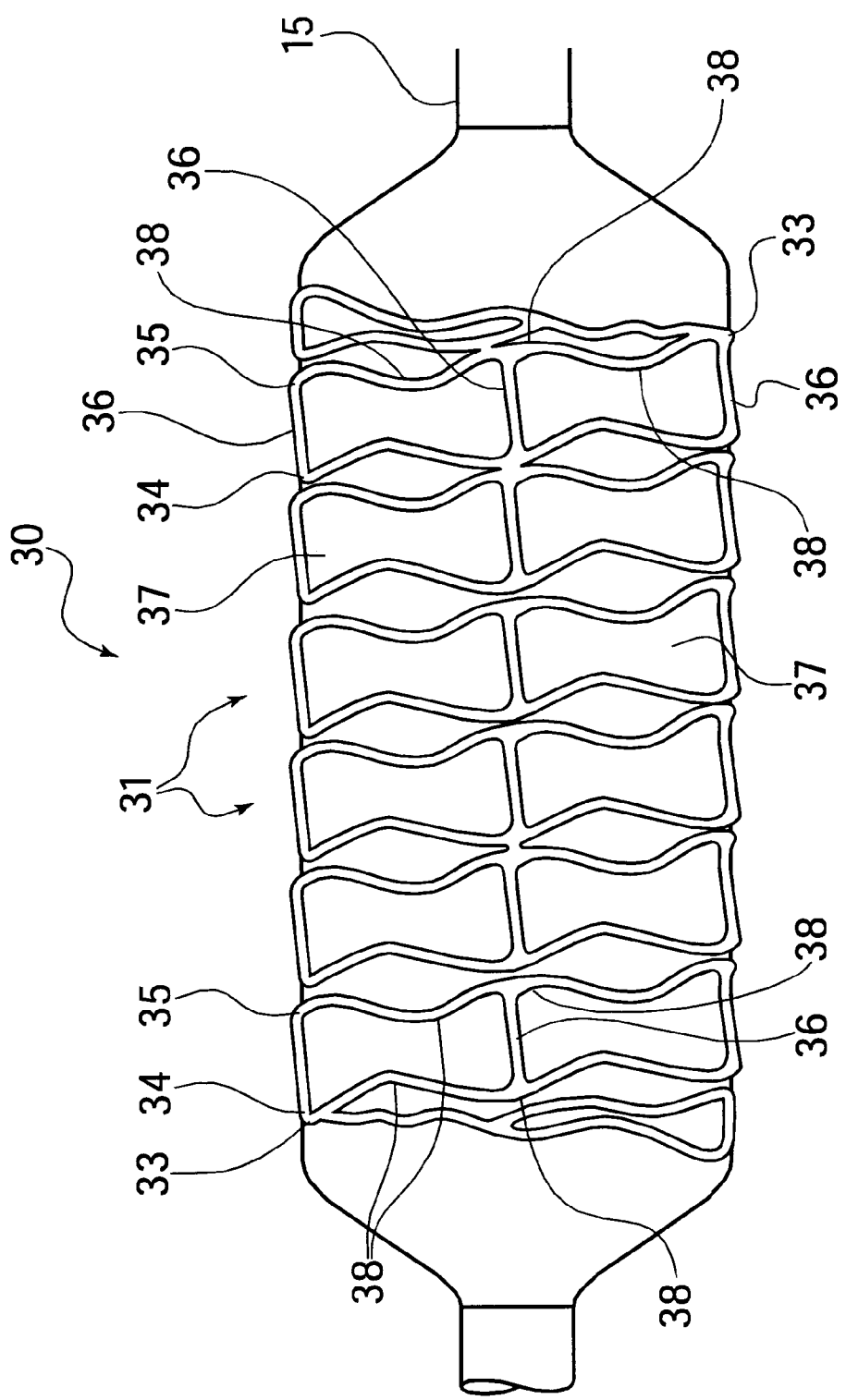
FIG. 5 shows a serpentine coiled ladder stent in accordance with the invention, in an expanded condition.

FIG. 5 shows a serpentine coiled ladder stent 30 constructed in accordance with the invention. The serpentine coiled ladder stent 30 in FIG. 5 is shown mounted on a catheter 15, in an expanded condition.

The serpentine coiled ladder stent 30 illustrated in FIG. 5 is configured as a coiled stent in which the coil is formed from a wound strip of cells 37, wherein the sides of the cells 37 are serpentine. Thus, the stent is comprised of a strip helically wound into a series of coiled windings 31, wherein the strip is formed of two side bands 34, 35 connected to each other, for example by a series of cross struts 36. Each side band 34, 35 is formed in a serpentine pattern comprising a series of bends 38, wherein upon expansion of the stent, the bends 38 of the side bands 34, 35 open to increase the length of each of the individual cells 37 in the helical direction, thereby lengthening the strip in the helical direction to allow the stent 30 to expand without any significant unwinding of the strip. In this illustrated embodiment, the bends in the side bands 34, 35 occur in a periodic pattern. The bends 38 may be arranged, for example, in the pattern of a sine wave, or in any other suitable configuration.

Alternatively, the stent may be described as a series of square cells 37. The side bands 34, 35 and the cross struts 36 form the perimeter of each cell. In the unexpanded state, the side bands are collapsed to form a serpentine continuum.

In the illustrated embodiment, the cross struts 36 joining the side bands 34, 35 to each other are straight and extend in a direction generally perpendicular to the helical direction in which the strip is wound. Alternatively, the cross struts may have one or more bends, and/or they may extend between the two side bands at other angles. In the illustrated embodiment, the cross struts 36 join oppositely facing bends 38 on the side bands 34, 35, and they are attached to the side bands 34, 35 at every second bend 38. Alternatively, the cross struts 36 may be joined in other places, and may occur with more or less frequency, without departing from the general concept of the invention. The stent alternatively may be made without cross struts 36, by having the two serpentine side bands 34, 35 periodically joined to each other at adjacent points.

As shown in FIG. 5, the ends 33 of the serpentine ladder strip may be tapered. The tapering of the ends 33 of the strip allows the ends of finished stent to be straight, i.e., it allows the stent to take the form of a right cylinder, with each of the ends of the cylindrical stent lying in a plane perpendicular to the longitudinal axis of the stent. The ends 33 of the strip may be joined, for example by welds, to respective adjacent windings 31.

Figure 6:
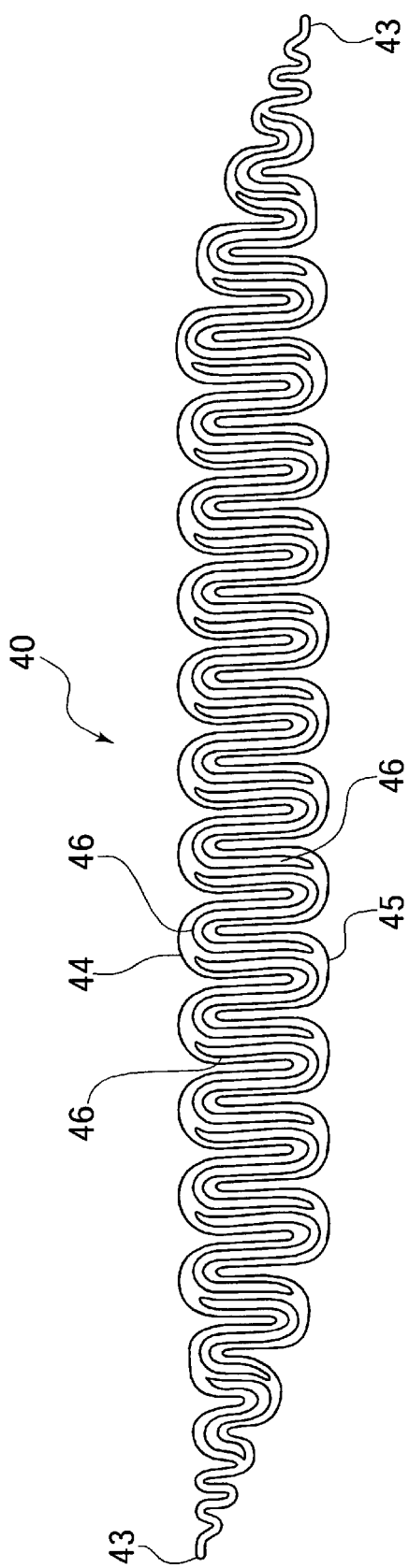
FIG. 6 shows a strip used to form a serpentine coiled ladder stent in accordance with the invention.

FIG. 6 shows a strip 40 used to form a serpentine coiled ladder stent in accordance with the invention. The strip 40 has serpentine side bands 44, 45, joined by cross struts 46. The strip 40 is tapered at its ends, such that the serpentine side bands 44, 45 converge at ends 43.

Figure 7:
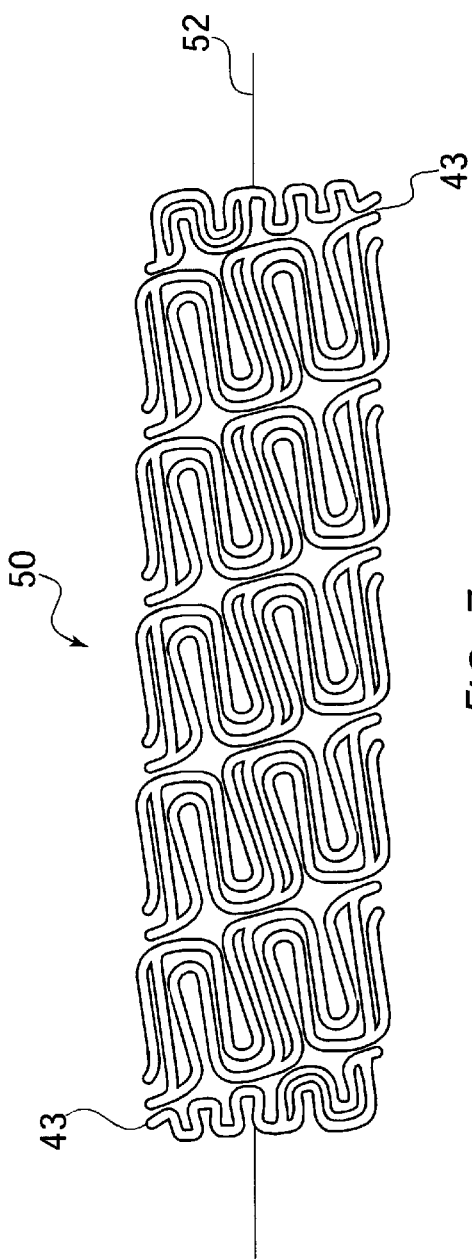
FIG. 7 shows a serpentine coiled ladder stent in accordance with the invention, in an unexpanded condition.

FIG. 7 shows a serpentine coiled ladder stent 50 constructed from the strip 40, in an unexpanded condition. As shown in FIG. 7, the tapered ends 43 may be joined to the respective adjacent windings. Also, the cross struts of the stent of FIG. 7 are positioned slightly askew to the longitudinal axis 52 of the stent 50.

Figure 8:
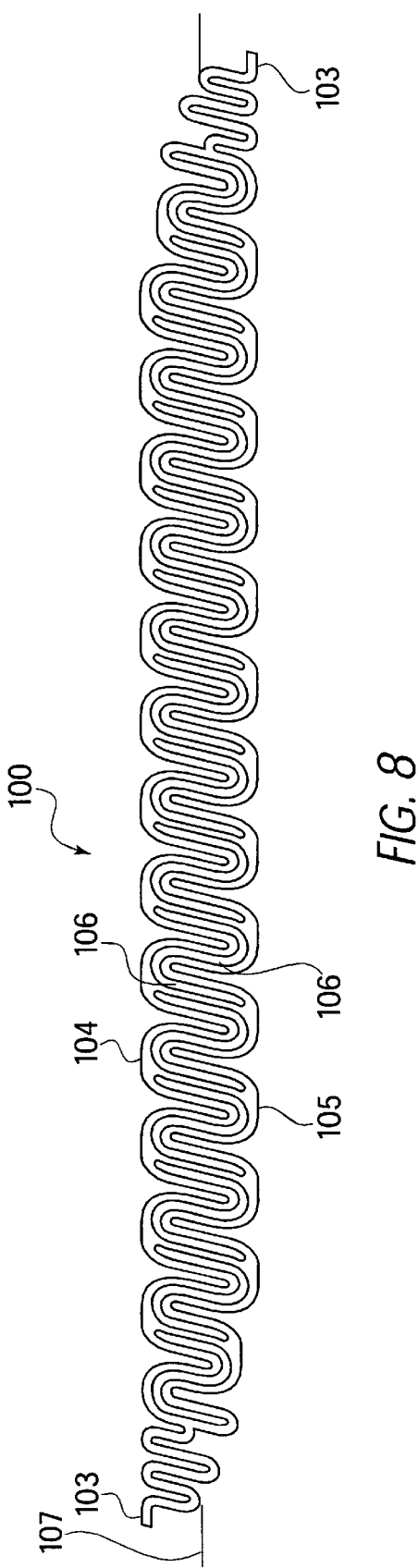
FIG. 8 shows a strip used to form a serpentine coiled ladder stent in accordance with the invention.

FIG. 8 shows an alternative strip 100 used to form a serpentine coiled ladder stent in accordance with the invention. The strip 100 has serpentine side bands 104, 105 joined by cross struts 106. The strip 100 is tapered at its ends, such that the serpentine side bands 104, 105 converge at ends 103. The cross struts 106 are positioned slightly askew. In other words, the cross struts are not exactly perpendicular to the longitudinal axis 107 of the strip 100. Accordingly, when a stent is constructed from the strip 100, the cross struts 106 will be positioned parallel to the longitudinal axis of the stent that is formed.

When the serpentine coiled ladder stent is expanded, as shown in FIG. 5, the outward radia force on the stent causes the bends 38 in the serpentine sides 34, 35 to open, thereby causing the length of the cells 37 to increase in the helical direction. This feature of the expandable cells of the strip allows the overall length of the strip to increase in the helical direction. By the strip itself lengthening in the helical direction as the stent is expanded, the increase in the diameter of the stent is accommodated without the need for the strip to unwind. In this manner, the number of windings 31 is maintained, and rotation of the ends 33 is avoided. In fact, because the ends 33 do not rotate, they may be welded, as mentioned above, to the respective adjacent windings 31, thereby creating smooth ends. Other adjacent points on the stent windings 31 may similarly be joined, to increase stability of the stent at the expense of flexibility.

A serpentine coiled ladder stent according to the invention retains the flexibility associated with coiled wire stents, but avoids some of the problems associated with those stents. The windings of the serpentine coiled ladder stent are relatively stable and insusceptible to displacement or tilting, which has been associated not only with straight single strand coiled stents as in the Maass '545 patent but also with serpentine single strand coiled stents, such as in the Wiktor '062 and '732 patents and in the Cordis Crossflex stent. In addition, a serpentine coiled ladder stent according to the invention provides continuous support of the vessel tissue without a disadvantageously high percentage of metal coverage. Because the strip from which the stent is made can expand in length in the helical direction, the strip can lengthen on expansion to accommodate the increased diameter, thereby substantially avoiding the problems of end rotation and foreshortening or the opening of significant gaps between windings upon expansion.

The strip for forming the serpentine coiled ladder stent may be made, for example, of wire or flat metal. When flat metal is used, the pattern in the strip may be formed, for example, by laser cutting or chemical etching. The stent may be manufactured by first manufacturing the strip, then winding the strip in a helix to form the stent, and then, if desired, welding the ends of the strip to the adjacent windings. Alternatively, the stent may be formed by forming the desired pattern directly out of a tube, by laser cutting or chemical etching, or by forming the desired pattern out of a flat sheet, by laser cutting or chemical etching, and then rolling that flat sheet into a tube and joining the edges, for example by welding. Any other suitable manufacturing method known in the art may be employed for manufacturing a stent in accordance with the invention.

The embodiments described herein are examples only, as other variations are within the scope of the invention as defined by the appended claims.

What is claimed is:

1. A stent comprised of a strip helically wound into a series of coiled windings, the strip having a longitudinal axis, wherein the strip has at least two side bands, wherein each of the at least two side bands is formed in a serpentine pattern comprising a series of bends, wherein the at least two side bands of the strip are connected to each other by cross struts, wherein the cross struts are not perpendicular to the longitudinal axis of the strip, and wherein upon expansion of the stent, the bends of the at least two side bands open to lengthen the strip in the helical direction to allow the stent to expand without any significant unwinding of the strip.

2. A stent as claimed in claim 1, wherein the cross struts connect adjacent bends on the at least two serpentine side bands.

3. A stent as claimed in claim 2, wherein the adjacent bends that are connected by each cross strut face in opposite directions.

4. A stent as claimed in claim 2, wherein the cross struts connect the at least two serpentine side bands at periodic intervals, and wherein each of the at least two serpentine side bands has at least one bend between sequential cross struts.

5. A stent as claimed in claim 1, wherein the cross struts are straight.

6. A stent as claimed in claim 1, wherein the cross struts have bends.

7. A stent as claimed in claim 1, wherein the strip has two ends, wherein the at least two side bands converge toward each other at the two ends of the strip, so that the two ends of the strip are tapered.

8. A stent as claimed in claim 1, wherein the strip has two ends, the first end of the strip being located at a first end of the stent and the second end of the strip being located at a second end of the stent, and wherein each end of the strip is joined to an adjacent winding of the stent.

9. A stent as claimed in claim 8, wherein each end of the strip is joined to the adjacent winding by welding.

10. A stent as claimed in claim 1, wherein the strip is made of wire.

11. A stent as claimed in claim 1, wherein the strip is made from flat metal.

12. A stent as claimed in claim 1, wherein the stent is made by manufacturing the strip and then winding the strip in a helix to form the stent.

13. A stent as claimed in claim 1, wherein the stent is made by etching the strip out of a tube.

14. A strip used to form a helically wound stent, comprising at least two side bands formed in a serpentine pattern; and cross struts connecting the side bands, wherein the cross struts are slightly askew to a direction perpendicular to a longitudinal axis of the strip.

15. The strip according to claim 14, wherein when the strip is helically wound to form a stent, the cross struts are parallel to a longitudinal axis of the stent.

16. A strip according to claim 14, wherein the strip is made of wire.

17. A strip according to claim 14, wherein the strip is made from flat metal.

18. A stent comprised of a strip helically wound into a series of coiled windings, wherein the strip is formed from a series of square cells, and wherein in the unexpanded state, the sides of the square cells are collapsed to form a serpentine continuum.

19. A stent as claimed in claim 18, wherein the sides of the square cells are formed from side bands formed in a serpentine pattern.

20. A stent as claimed in claim 19, wherein the side bands are connected by cross-struts.

* * * * *

UNITED STATES PATENT AND TRADEMARK OFFICE
CERTIFICATE OF CORRECTION

PATENT NO.    : 6,503,270 B1   Page 1 of 1
DATED         : January 7, 2003
INVENTOR(S)   : Richter, Jacob et al.

It is certified that error appears in the above-identified patent and that said Letters Patent is hereby corrected as shown below:

<u>Column 6,</u>
Line 29, "radia" should read -- radial --

Signed and Sealed this

Eleventh Day of November, 2003

JAMES E. ROGAN
*Director of the United States Patent and Trademark Office*